US008889924B2

(12) United States Patent
Nair et al.

(10) Patent No.: US 8,889,924 B2
(45) Date of Patent: Nov. 18, 2014

(54) PROCESS FOR THE PRODUCTION OF 1,3,3,3-TETRAFLUOROPROPENE

(71) Applicant: Honeywell International Inc., Morristown, NJ (US)

(72) Inventors: Haridasan K. Nair, Williamsville, NY (US); Rajiv Ratna Singh, Getzville, NY (US); Andrew Joseph Poss, Kenmore, NY (US); David Nalewajek, West Seneca, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 13/757,911

(22) Filed: Feb. 4, 2013

(65) Prior Publication Data

US 2013/0211156 A1 Aug. 15, 2013

Related U.S. Application Data

(60) Provisional application No. 61/598,523, filed on Feb. 14, 2012.

(51) Int. Cl.
| C07C 17/25 | (2006.01) |
| C07C 17/278 | (2006.01) |
| C07C 19/01 | (2006.01) |
| C07C 19/08 | (2006.01) |
| C07C 19/10 | (2006.01) |
| C07C 21/06 | (2006.01) |
| C07C 21/18 | (2006.01) |
| C07C 17/20 | (2006.01) |

(52) U.S. Cl.
CPC .............. *C07C 17/25* (2013.01); *C07C 17/278* (2013.01); *C07C 21/06* (2013.01); *C07C 19/08* (2013.01); *C07C 17/206* (2013.01); *C07C 19/10* (2013.01)
USPC ........... 570/155; 570/156; 570/157; 570/136; 570/167; 570/168; 570/170; 570/171; 570/172; 570/219; 570/237; 570/242

(58) Field of Classification Search
CPC ...... C07C 17/25; C07C 17/206; C07C 19/10; C07C 19/08; C07C 17/21; C07C 17/278; C07C 21/06; C07C 21/04

USPC ......... 570/156, 155, 157, 136, 153, 164, 169, 570/227, 226, 170, 166, 167, 168, 175, 171
See application file for complete search history.

(56) References Cited

U.S. PATENT DOCUMENTS

| 5,986,151 | A | 11/1999 | Van Der Puy | |
| 6,124,510 | A | 9/2000 | Elsheikh et al. | |
| 6,500,995 | B1 * | 12/2002 | Branam | 570/257 |
| 6,548,719 | B1 | 4/2003 | Nair et al. | |
| 7,803,973 | B2 * | 9/2010 | Merkel et al. | 570/156 |
| 7,829,748 | B1 * | 11/2010 | Tung et al. | 570/164 |
| 2005/0020862 | A1 * | 1/2005 | Tung et al. | 570/164 |
| 2007/0129580 | A1 | 6/2007 | Mukhopadhyay et al. | |
| 2008/0091053 | A1 * | 4/2008 | Tung et al. | 570/153 |

FOREIGN PATENT DOCUMENTS

| JP | 2012020992 A * | 2/2012 |
| WO | 2005-108332 | 11/2005 |
| WO | WO 2010101198 A1 * | 9/2010 |
| WO | 2011-034991 | 4/2011 |

OTHER PUBLICATIONS

Nose, M. Patent No. JP2012020992, English translation.*
Nose, M. Patent No. JP2012020992, English translation, Feb. 2, 2012.*
PCT Search Report & Written Opinion from PCT/US2013/025243 dated May 8, 2013.

* cited by examiner

*Primary Examiner* — Fereydoun G Sajjadi
*Assistant Examiner* — Medhanit Bahta
(74) *Attorney, Agent, or Firm* — Erika S. Wilson

(57) ABSTRACT

The present invention provides a simple three step process for the production of 1,3,3,3-tetrafluoropropene (HFO-1234ze). In the first step, carbon tetrachloride is added to vinyl fluoride to afford the compound $CCl_3CH_2CHClF$ (HCFC-241fb). HCFC-241fb is then fluorinated with anhydrous HF to afford $CF_3CH_2CHClF$ (HCFC-244fa) in the second step. Dehydrochlorination of HCFC-244fa, in the third step, affords the desired product, $CF_3CH\!\!=\!\!CHF$ (HFO-1234ze). Following similar chemistry, vinyl chloride may be used in place of vinyl fluoride.

16 Claims, No Drawings

PROCESS FOR THE PRODUCTION OF 1,3,3,3-TETRAFLUOROPROPENE

CROSS-REFERENCE TO RELATED APPLICATION

This application claims domestic priority under 35 U.S.C. 119(e) to commonly owned U.S. Provisional Application Ser. No. 61/598,523, filed 14 Feb. 2012, the disclosure of which is hereby incorporated herein by reference.

FIELD OF THE INVENTION

The present invention describes a process for making the compound 1,3,3,3-tetrafluoropropene ($CF_3CH=CHF$, HFO-1234ze or 1234ze). The described process is industrially applicable for making 1234ze from commercially available raw materials.

BACKGROUND OF THE INVENTION

The tetrafluoropropene compound 1234ze is a useful compound with low global warming potential which is used in many applications. For example, $CF_3CH=CHF$ is useful as a foam blowing agent, refrigerant, and as monomer for homopolymers and copolymers.

Several methods for the preparation of $CF_3CH=CHF$ are known. For example, U.S. Pat. No. 6,548,719 describes the production of many fluoro-olefins including $CF_3CH=CHF$ from $CF_3CH_2CF_2H$ (245fa) by dehydrohalogenation in the presence of a phase transfer catalyst. U.S. Pat. Nos. 5,986,151 and 6,124,510 describe the gas phase catalytic dehydrofluorination of $CF_3CH_2CF_2H$ to afford $CF_3CH=CHF$. These documents are hereby incorporated herein by reference.

Gas phase dehydrochlorination of $CF_3CH_2CHFCl$ (244fa) is reported to give $CF_3CH=CHF$ as described in U.S. Pat. No. 7,829,748. Vapor phase fluorination of $CF_3CH=CHCl$ (1233zd) with HF with $SbF_5$ catalyst affords HFO-1234ze along with 245fa. See, for example, U.S. Pat. No. 7,829,748. This document is hereby incorporated herein by reference.

The main disadvantages of the above described methods are that in each case the starting materials, for example $CF_3CH_2CF_2H$, typically need to be made in multiple reaction steps, and/or with relatively expensive raw materials, and thus there is a need to provide an improved (or alternate) process for the production of HFO-1234ze, at least from a cost effectiveness viewpoint. Accordingly, the present invention has been developed, namely a process which utilizes relatively inexpensive and commercially available starting materials for making HFO-1234ze as detailed below.

SUMMARY OF THE INVENTION

The present invention provides a simple three step process for the production of 1,3,3,3-tetrafluoropropene (HFO-1234ze). In the first step, carbon tetrachloride is added to vinyl fluoride to afford the compound $CCl_3CH_2CHClF$ (HCFC-241fb). HCFC-241fb is then fluorinated with anhydrous HF to afford $CF_3CH_2CHClF$ (HCFC-244fa) in the second step. Dehydrochlorination of HCFC-244fa, in the third step, affords the desired product, $CF_3CH=CHF$ (HFO-1234ze).

One embodiment of the present invention provides a simple three step process as depicted below:

$$CH_2=CHF+CCl_4 \rightarrow CCl_3CH_2CHClF \quad (1)$$

(addition)

$$CCl_3CH_2CHClF \rightarrow CF_3CH_2CHClF \quad (2)$$

(HF)

$$CF_3CH_2CHClF \rightarrow CF_3CH=CHF \quad (3)$$

(−HCl)

In another embodiment, vinyl chloride can be used in place of vinyl fluoride, such that the process has the following three steps:

$$CCl_4+CH_2=CHCl \rightarrow CCl_3CH_2CHCl_2 \quad (1)$$

$$CCl_3CH_2CHCl_2 \rightarrow CF_3CH_2CFHCl \quad (2)$$

$$CF_3CH_2CFHCl \rightarrow CF_3H=CHF \quad (3)$$

DETAILED DESCRIPTION OF THE INVENTION

As shown in the above depicted reactions, the process comprises three steps:

Step (1)—addition of carbon tetrachloride to vinyl fluoride/chloride,

Step (2)—fluorination of the resultant product with HF, and

Step (3)—dehydrochlorination of the compound from step (2).

Thus, in one embodiment of the first step, carbon tetrachloride is added to vinyl fluoride to afford compound $CCl_3CH_2CHClF$ (HCFC-241fb) which is then fluorinated with HF, preferably anhydrous HF, to afford $CF_3CH_2CHClF$ (HCFC-244fa) in the second step. Fluorination reactions are typically carried out with hydrogen fluoride, preferably anhydrous HF (AHF) and a fluorination catalyst. These catalysts are well known, and one can fine tune the reaction conditions to afford mainly the desired product. Dehydrochlorination of $CF_3CH_2CHClF$ (HCFC-244fa), in the third step, affords $CF_3CH=CHF$ (HFO-1234ze).

In certain embodiments, the addition reaction of $CCl_4$ to $CH_2=CHF$ was conducted in the presence of triethylphosphate and iron powder at elevated temperature (120° C. to 130° C.) to afford $CCl_3CH_2CHClF$ (HCFC-241fb), in good yield.

Iron nano particles and/or nano powder, which are commercially available, can also be employed for the addition reaction instead of iron powder. Iron nano particles can be on a support such as activated carbon. The advantage of Fe nanopowder is its large surface area thus reducing its amount as well as time required for the reaction.

In certain embodiments, the HCFC-241fb was fluorinated with three (3) equivalents of anhydrous HF in the presence of a fluorination catalyst such as $SbCl_5$ to afford $CF_3CH_2CHClF$ (see for example U.S. Pat. No. 7,829,748). By-products such as $CF_3CH=CHCl$ (HCFO-1233zd) or $CF_3CH=CHF$ (HFO-1234ze) which may be formed can easily be separated from the higher boiling HCFC-244fa, for example, by distillation. Also, the fluorination reaction conditions may be fine-tuned in such a way that the desired $CF_3CH_2CHClF$ is predominantly obtained.

In certain embodiments, the fluorination reaction is carried out in a Monel® tube reactor which is charged with a premade fluorination catalyst such as $SbCl_5$ (or $SbF_5$ or $SbCl_xF_y$, where x+y=5) on activated carbon (Togo Calgon PCB, 4×10 mesh) and heated to about 70° C. to 85° C. (see U.S. Pat. No. 7,829,748). Then a mixture of vaporized $CCl_3CH_2CHClF$ and anhydrous HF (AHF) in a ratio of about 1:10 is passed through the heated catalyst bed in the reactor with a contact time of from 2 sec to 10 sec. Contact time=bulk volume of catalyst/volumetric flow rate of reactants in ml/sec. The flow rate of each reactant was controlled with a mass flow meter/controller in such a way that the contact time is maintained in the range of 2 sec. to 10 sec.

The effluent from the reactor was analyzed by GC/GC-MS for identification the products. $CF_3CH_2CHClF$ (HCFC-244fa) was obtained as the main product; the by-products were $CF_3CH_2CF_2H$ (HFC-245fa) and $CF_3CH=CHCl$ (HCFC-1233zd) which could easily be separated from the higher boiling HCFC-244fa (bp=30° C. at 27 psi) by distillation.

Dehydrochlorination of $CF_3CH_2CHClF$ can either be carried out in liquid or gas phase with an appropriate catalyst, as taught for example, in U.S. Patent Pub. No. 2007-0129580, U.S. Pat. No. 7,829,748 and PCT Publication No. WO 2009/0211542. Many catalysts can be used for dehydrochlorination depending on the reaction conditions. For liquid phase reactions, typical catalysts are sodium or potassium hydroxide with a phase transfer catalyst, as taught in U.S. Pat. No. 7,829,748. These documents are hereby incorporated herein by reference.

In certain embodiments, the vapor phase dehydrochlorination is conducted at a temperature range of from about 300° C. to 500° C. This process can be effected with a number of catalysts, including for example, acid treated activated carbon, or a mixture metal chloride and metal fluoride catalysts, for example $CsCl+MgF_2$ in a 1:9 ratio.

All processes described here can be run in a continuous manner either individually or as a combination of some or all of the individual process steps. As will be appreciated by those having ordinary skill in this art, various reaction modifications can be implemented for better selectivity and yield in each of the reaction steps described herein.

EXAMPLES

Example 1

Addition of $CCl_4$ to $CH_2=CHF$

To a clean, dry and leak tested 1 L autoclave was added iron powder (5.0 g, 89 mmol), triethylphosphate (22.5 g, 89 mmol) and carbon tetrachloride (425 g, 2.76 mol) under nitrogen purge. The autoclave was purged with nitrogen for 3 minutes and evacuated. To the evacuated autoclave was introduced vinyl fluoride (157 g, 2.70 mol), and the pressure was from about 58 psi to 60 psi. The stirred contents in the autoclave were then heated to and maintained at a temperature from 120° C. to 125° C. for 8 hours at a pressure about 120 psi.

An additional 10 g of triethylphosphate (39 mmol) was injected into the autoclave and heated for additional 10 hours at 120° C. to 125° C. The autoclave was cooled to 25° C. and the contents were poured into cold water (about 1 L), the organic layer separated, washed thrice with water, dried over $MgSO_4$ and filtered. The crude material was distilled at 63° C. to 65° C. to afford 470 g (yield=81%) of $CCl_3CH_2CHClF$.

Example 1a

The reaction of Example 1 was again carried out except that Fe nano powder (2.0 g, 36 mmol) and triethyl phosphate (9.1 g, 36 mmol) were used and heated for 5 hrs at 120-130° C. at pressure of about 110 to 120 psi. The work up and isolation was the same as described for the above example; yield ranged from 60-85%.

Example 2

Fluorination of $CCl_3CH_2CHClF$ to $CF_3CH_2CFHCl$

The fluorination reaction was conducted in a Monel® tube reactor (2.54 cm diameter, 80 cm long). The reactor was then charged with 150 g of fluorination catalyst, as described in U.S. Pat. No. 7,829,748, $SbCl_5$ on activated carbon (Toyo Colon PCB, 4×10 mesh), and heated to 85° C. Then a mixture of vaporized $CCl_3CH_2CHClF$ and anhydrous HF (1:10) was passed through the heated catalyst with a contact time of from 2 sec. to 10 sec. Contact time=bulk volume of catalyst/volumetric flow rate of reactants in ml/sec. The flow rate of each reactant was controlled with a mass flow meter-controller in such a way that the contact time was in the range of from 2 sec. to 10 sec.

The effluent mainly consisted of $CF_3CH_2CHClF$ (HCFC-244fa). For example, with a contact time of 2 sec., at 65° C. to 70° C., the yield of $CF_3CH_2CHClF$ ranged from 40% to 50% as determined by GC area; the remainder being by-products including $CF_3CH_2CF_2H$ (HFC-245fa) and $CF_3CH=CHCl$ (HCFC-1233zd) about 1:1, HCFC-244fa which were separated by distilling.

Example 3

Dehydrochlorination of $CF_3CH_2CHClF$

A. Liquid Phase:

Into a 0.5 L Teflon lined autoclave was charged 300 g of 20% aq. KOH solution, 1 g Aliquat 336 or 18-crown ether and 20 g $CF_3CH_2CHClF$. The contents in the autoclave were heated to and maintained at from 50° C. to 55° C. for 6 hours. The progress of the reaction was monitored by GC. After 12 hours, the product HFO-1234ze (65% yield) was collected in a steel cylinder cooled at −78° C.

B. Vapor phase:

In a Monel tube reactor, 20 cc of acid treated (HCl or $HNO_3$) catalyst was loaded and heated to 350° C. to 370° C. Then vapor stream of $CF_3CH_2CHClF$ at a rate about 6 g/h was passed through the heated catalyst bed in the reactor for from 1 hour to 8 hours. The conversion of HCFC-244fa ranged from 40% to 60% with a selectivity of HFO-1234ze greater than 95%. Further purification was accomplished by distillation.

Example 4

Addition of $CCl_4$ to $CH_2=CHCl$

This reaction was conducted in essentially the same manner as Example 1, except for the fact that instead of vinyl fluoride, an equivalent amount of vinyl chloride was used for the reaction. After work up and distillation, 65% yield of $CCl_3CH_2CHCl_2$ was obtained.

Example 5

Reaction of $CCl_3CH_2CHCl_2$ with HF

This reaction was carried out in a 1 gallon Hastelloy C reactor by reacting $CCl_3CH_2CHCl_2$ with HF using $TiCl_4$ as the catalyst. Typically, 1.4 lb of anhydrous HF and 0.15 lbs of $TiCl_4$ was added to the reactor; HCl was formed immediately which was vented and passed through a scrubber. After venting HCl gas 5 lbs of $CCl_3CH_2CHCl_2$ was added and the reactor was heated to 85° C. and the system pressure was maintained at around 120 psig. Additional HF was then added and the product was stream was collected in cold trap.

The products formed, as analyzed by GC, are $CF_3CH=CHF$, as well as $CF_3CH_2CHClF$, $CF_3CH=CHCl$, and $CF_3CH_2CF_2H$. The reaction conditions were fine-tuned such that the major products were $CF_3CH=CFH$, $CF_3CH_2CHClF$ (combined 50%) besides the other by-products. The $CF_3CH=CFH$ thus formed was separated by distillation and the $CF_3CH2CHClF$ is dehydrochlorinated to $CF_3CH=CFH$ as described in Example 3.

Alternately, 240fa can be passed through a Monel or nickel tube reactor with HF (10 to 20 fold excess) over a catalyst such as metal powder for example Al, Zn, Mg, Ni, Ti, Co on carbon support at elevated temperature (200° C. to 500° C.) with a contact time of 5 sec. to 20 sec. The reaction conditions temperature, contact time, flow rate of $CCl_3CH_2CHCl_2$ and HF are fine-tuned and selected with few runs such that the main product formed is $CF_3CH=CHF$.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A process for the production of 1,3,3,3-tetrafluoropropene (HFO-1234ze) comprising the continuous steps of:
   (a) reacting carbon tetrachloride with vinyl fluoride to afford a yield of up to about 60% by weight of the compound $CCl_3CH_2CHClF$ (HCFC-241fb);
   (b) fluorinating the HCFC-241fb formed in step (a) with an excess amount of HF in the presence of a fluorination catalyst to afford a yield of up to about 40% by weight of the compound $CF_3CH_2CHClF$ (HCFC-244fa); and
   (c) dehydrochlorinating the HCFC-244fa formed in step (b) to produce a yield of up to about 40% by weight of the compound $CF_3CH=CHF$ (HFO-1234ze);
   wherein the reaction of carbon tetrachloride with the vinyl halide compound is conducted in the presence of triethylphosphate and an iron material selected from the group consisting of supported or unsupported iron powder, iron nanopowder and iron nanoparticles, at a temperature of from about 120° C. to 130° C.

2. The process of claim 1, wherein at least three equivalents of hydrogen fluoride are used.

3. The process of claim 1, wherein the hydrogen fluoride is anhydrous.

4. The process of claim 1, wherein fluorination catalyst has the formula $SbCl_xF_y$, wherein x+y=5.

5. The process of claim 4, wherein fluorination catalyst comprises $SbCl_5$.

6. The process of claim 4, wherein fluorination catalyst comprises $SbF_5$.

7. The process of claim 1, wherein any by-products formed during the fluorination reaction are separated from the HCFC-244fa.

8. The process of claim 7, wherein one by-product comprises the compound $CF_3H=CHCl$ (HCFO-1233zd).

9. The process of claim 7, wherein one by-product comprises the compound $CF_3CH=CHF$ (HFO-1234ze).

10. The process of claim 1, wherein the dehydrochlorination reaction of $CF_3CH_2CHClF$ is conducted in either the liquid phase or the gas phase, with a dehydrochlorination catalyst.

11. The process of claim 10, wherein the dehydrochlorination reaction is conducted in the liquid phase.

12. The process of claim 10, wherein the dehydrochlorination reaction is conducted in the gas phase.

13. The process of claim 11, wherein the catalyst is selected from the group consisting of sodium or potassium hydroxide with a phase transfer catalyst.

14. The process of claim 12, wherein the catalyst is selected from the group consisting of acid treated activated carbon, and a mixture metal chloride and metal fluoride catalysts.

15. The process of claim 14, wherein the catalyst comprises $CsCl+MgF_2$ in a 1:9 ratio.

16. The process of claim 12, wherein the dehydrochlorination reaction is conducted at a temperature range of from about 300° C. to 500° C.

* * * * *